US012740983B2

(12) United States Patent
Hu et al.

(10) Patent No.: US 12,740,983 B2
(45) **Date of Patent: *Sep. 22, 2026**

(54) CDK INHIBITORS

(71) Applicant: GENENTECH, INC., South San Francisco, CA (US)

(72) Inventors: Zhilong Hu, Shanghai (CN); Hu He, Shanghai (CN); Fei Zhang, Shanghai (CN); Wenge Zhong, Thousand Oaks, CA (US); Xiaotian Zhu, Newton, MA (US)

(73) Assignee: GENENTECH, INC., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/210,611

(22) Filed: May 16, 2025

(65) Prior Publication Data

US 2025/0275971 A1 Sep. 4, 2025

Related U.S. Application Data

(60) Continuation of application No. 18/785,844, filed on Jul. 26, 2024, which is a division of application No. 17/922,804, filed as application No. PCT/US2021/030728 on May 4, 2021, now Pat. No. 12,285,429.

(30) Foreign Application Priority Data

May 5, 2020 (WO) ................ PCT/CN2020/088585

(51) Int. Cl.

| | |
|---|---|
| ***C07D 401/14*** | (2006.01) |
| ***A61K 31/506*** | (2006.01) |
| ***A61K 31/5377*** | (2006.01) |
| ***A61K 31/55*** | (2006.01) |
| ***A61K 45/06*** | (2006.01) |
| ***A61P 35/00*** | (2006.01) |
| ***C07D 405/14*** | (2006.01) |
| ***C07D 487/04*** | (2006.01) |

(52) U.S. Cl.

CPC ........ *A61K 31/506* (2013.01); *A61K 31/5377* (2013.01); *A61K 31/55* (2013.01); *A61K 45/06* (2013.01); *A61P 35/00* (2018.01); *C07D 401/14* (2013.01); *C07D 405/14* (2013.01); *C07D 487/04* (2013.01)

(58) Field of Classification Search

CPC .............. A61K 31/506; A61K 31/5377; A61K 31/55; A61K 45/06; A61K 31/551; A61K 31/553; A61K 2300/00; A61P 35/00; C07D 401/14; C07D 405/14; C07D 487/04; C07D 471/04; C07D 519/00; C07D 471/10

See application file for complete search history.

(56) References Cited

U.S. PATENT DOCUMENTS

| | | | |
|---|---|---|---|
| 6,194,410 | B1 | 2/2001 | Bos et al. |
| 7,855,211 | B2 | 12/2010 | Coates et al. |
| 7,977,477 | B2 | 7/2011 | Berdini et al. |
| 8,791,136 | B2 | 7/2014 | Goff et al. |
| 8,809,370 | B2 | 8/2014 | Goff et al. |
| 8,980,921 | B2 | 3/2015 | Goff et al. |
| 8,987,303 | B2 | 3/2015 | Goff et al. |
| 9,266,856 | B2 | 2/2016 | Goff et al. |
| 9,663,496 | B2 | 5/2017 | Irving et al. |
| 9,969,719 | B2 | 5/2018 | Ding et al. |
| 10,370,371 | B2 | 8/2019 | Du et al. |
| 10,377,742 | B2 | 8/2019 | Goff et al. |
| 10,464,927 | B2 | 11/2019 | Zheng et al. |
| 10,941,134 | B2 | 3/2021 | Goff et al. |
| 11,352,351 | B2 | 6/2022 | Jin et al. |
| 11,427,548 | B2 | 8/2022 | Crew et al. |
| 2004/0248903 | A1 | 12/2004 | Gudmundsson et al. |
| 2005/0049260 | A1 | 3/2005 | Boyd et al. |
| 2009/0221597 | A1 | 9/2009 | Ruah et al. |
| 2019/0071427 | A1 | 3/2019 | Zheng et al. |

(Continued)

FOREIGN PATENT DOCUMENTS

| | | |
|---|---|---|
| CA | 2956628 | 2/2016 |
| CA | 107286134 | 10/2017 |

(Continued)

OTHER PUBLICATIONS

Gura et al (Science, 1997, 278:1041-1042) (Year: 1997).*
Johnson et al (British Journal of Cancer, 2001, 84:1424-1431) (Year: 2001).*
Kunnumakkara et al (Experimental Biology and Medicine, 2019; 244:663-689) (Year: 2019).*
Hope et al (RSC Chem. Biol., 2023; 4:146-164) (Year: 2023).*
Caira, M., "Crystalline Polymorphism of Organic Compounds", Topics in Current Chemistry, 198:163-208, 1998, 46 pages.

(Continued)

*Primary Examiner* — Rayna Rodriguez
(74) *Attorney, Agent, or Firm* — Norton Rose Fulbright US LLP

(57) ABSTRACT

The invention provides a compound represented by represented by the following structural formula:

, or a pharmaceutically acceptable salt, or a stereoisomer thereof useful for treating cancer.

2 Claims, No Drawings

(56) References Cited

U.S. PATENT DOCUMENTS

| | | | |
|---|---|---|---|
| 2022/0296595 A1 | 9/2022 | Hu et al. |
| 2023/0174512 A1 | 6/2023 | Hu et al. |
| 2024/0033264 A1 | 2/2024 | Hu et al. |
| 2024/0066031 A1 | 2/2024 | Hu et al. |

FOREIGN PATENT DOCUMENTS

| | | |
|---|---|---|
| CA | 108484606 | 9/2018 |
| CN | 104761544 | 7/2015 |
| CN | 105732615 A | 7/2016 |
| CN | 105732615 B | 5/2018 |
| CN | 109503573 | 3/2019 |
| CN | 109952295 A | 6/2019 |
| CN | 109963842 A | 7/2019 |
| CN | 110156754 | 8/2019 |
| CN | 109963842 B | 11/2020 |
| CN | 112225724 A | 1/2021 |
| CN | 112250669 A | 1/2021 |
| CN | 109952295 B | 4/2021 |
| CN | 112250669 B | 2/2022 |
| CN | 112225724 B | 4/2022 |
| EP | 3269715 | 1/2018 |
| EP | 3444246 | 2/2019 |
| EP | 3620456 | 3/2020 |
| JP | 2009/542604 A | 12/2009 |
| KR | 10-2018- 0005160 | 1/2018 |
| WO | 1997/019065 | 5/1997 |
| WO | 2002/102783 | 12/2002 |
| WO | 2003/015776 | 2/2003 |
| WO | 2003/032997 | 4/2003 |
| WO | 2003/057165 | 7/2003 |
| WO | 2005/099711 | 10/2005 |
| WO | 2006/075152 | 7/2006 |
| WO | 2007/149427 | 12/2007 |
| WO | 2008/003766 | 1/2008 |
| WO | 2009/085185 | 7/2009 |
| WO | 2009/103032 | 8/2009 |
| WO | 2010/020675 | 2/2010 |
| WO | 2010/049731 | 5/2010 |
| WO | 2010/075074 | 7/2010 |
| WO | 2010/129053 | 11/2010 |
| WO | 2011/022440 | 2/2011 |
| WO | 2011/101409 | 8/2011 |
| WO | 2011/130232 | 10/2011 |
| WO | 2012/016217 | 2/2012 |
| WO | 2013/014448 | 1/2013 |
| WO | 2013/173506 | 11/2013 |
| WO | 2014/144740 | 9/2014 |
| WO | 2014/181287 | 11/2014 |
| WO | 2015/030847 | 3/2015 |
| WO | 2015/058163 | 4/2015 |
| WO | 2015/154039 | 10/2015 |
| WO | 2015/161285 | 10/2015 |
| WO | 2015/161287 | 10/2015 |
| WO | 2015/161288 | 10/2015 |
| WO | 2016/014881 | 1/2016 |
| WO | 2016/014904 | 1/2016 |
| WO | 2016/015605 | 2/2016 |
| WO | 2016/141881 | 9/2016 |
| WO | 2017/017783 | 2/2017 |
| WO | 2017/133701 | 8/2017 |
| WO | 2017/177836 | 10/2017 |
| WO | 2017/181177 | 10/2017 |
| WO | 2018/019204 | 2/2018 |
| WO | 2018/045956 | 3/2018 |
| WO | 2018/045957 | 3/2018 |
| WO | 2018/113771 | 6/2018 |
| WO | 2018/121766 | 7/2018 |
| WO | 2019/023553 | 1/2019 |
| WO | 2019/029663 | 2/2019 |
| WO | 2019/133864 | 7/2019 |
| WO | 2019/148161 | 8/2019 |
| WO | 2020/119739 | 6/2020 |
| WO | 2020/125513 | 6/2020 |
| WO | 2020/180959 | 9/2020 |
| WO | 2020/224568 | 11/2020 |
| WO | 2020/253862 | 12/2020 |
| WO | 2021/003517 | 1/2021 |
| WO | 2021/190637 | 9/2021 |

OTHER PUBLICATIONS

Yin et al., "A highly potent CDK4/6 inhibitor was rationally designed to overcome blood brain barrier in gliobastoma therapy", Eur J Med Chem., 144:1-28, 2018.

You, Medicinal Chemistry, 2nd Edition, China Medical Science and Technology Press, pp. 583-584, Feb. 28, 2011.

International Search Report and Written Opinion for Application No. PCT/CN2019/085494, dated Feb. 12, 2020, 12 pages.

International Search Report and Written Opinion for Application No. PCT/CN2020/088585, dated Jul. 29, 2020, 13 pages.

International Search Report and Written Opinion for Application No. PCT/CN2021/073515, dated Jun. 7, 2021, 8 pages.

International Search Report and Written Opinion for Application No. PCT/CN2024/132256, dated Feb. 5, 2025, 12 pages.

International Search Report and Written Opinion for Application No. PCT/US2021/030728, dated Jul. 2, 2021, 16 pages.

CAS Registry File 2118928-29-1, entered into STN Aug. 23, 2017, obtained from the internet Dec. 1, 2025 (Year: 2017).

Wu, Qing, et al. "Small-Molecule Inhibitors, Immune Checkpoint Inhibitors, and More: FDA-Approved Novel Therapeutic Drugs for Solid Tumors from 1991 to 2021." *Journal of Hematology & Oncology*, vol. 15, No. 1, 2022, p. 1-63.

* cited by examiner

CDK INHIBITORS

CROSS REFERENCE TO RELATED APPLICATION

This application is a Continuation application from U.S. patent application Ser. No. 18/785,844, filed Jul. 26, 2024, which is a Divisional application from U.S. patent application Ser. No. 17,922,804, filed Nov. 2, 2022, which is now U.S. Pat. No. 12,285,429, which is a 371 of PCT/US2021/030728, filed May 4, 2021, which claims the benefit of priority to International Patent Application Number PCT/CN2020/088585, filed on May 5, 2020. The entire contents of the aforementioned applications are incorporated herein by reference.

BACKGROUND OF THE INVENTION

Cyclin-Dependent Kinases (CDKs) are a family of protein kinases first discovered for their roles in regulating cell cycle. They have since been identified to play roles in regulating a number of other biological functions such as transcription, mRNA processing, and the differentiation of nerve cells.

CDKs are relatively small proteins with molecular weights between about 34-40 kDa. They contain little more than the kinase domain, and are essentially inactive when not in complex with a class of regulatory proteins called cyclins. CDK levels remain relatively constant throughout the cell cycle, and most regulation is post-translational, most prominently by binding to cyclins.

Like all kinases, the active site, or the ATP-binding site, of CDKs is a cleft between a small amino-terminal lobe and a larger carboxy-terminal lobe. The structure of human CDK2 revealed that CDKs have a modified ATP-binding site that can be regulated by cyclin binding. Phosphorylation by CDK-activating kinase (CAK) at Thr 161 on the T-loop increases the complex activity. Without cyclin, a flexible loop called the activation loop or T-loop blocks the cleft, and the position of several key amino acid residues is not optimal for ATP-binding. With cyclin, two alpha helices change position to permit ATP binding. One of them, the L12 helix that comes just before the T-loop in the primary sequence, becomes a beta strand and helps rearrange the T-loop, so it no longer blocks the active site. The other alpha helix called the PSTAIRE helix rearranges and helps change the position of the key amino acid residues in the active site.

Thus only the cyclin-CDK complex has active kinase activity, and most of known cyclin-CDK complexes regulate the progression through the cell cycle. The CDKs are ubiquitous in all known eukaryotes, and their regulatory function in the cell cycle has been evolutionarily conserved. For example, yeast cells can proliferate normally when their CDK gene has been replaced with the homologous human gene. CDKs exert their regulatory function by phosphorylating their substrates on certain specific Serine and Threonine residues, and the consensus sequence of [S/T]PX[K/R], where S/T is the target Ser or Thr for phosphorylation, P is proline, X is any amino acid, K is lysine, and R is arginine.

In animal cells, there are at least nine different CDKs, four of which (CDK1, 2, 3, and 4) are directly involved in cell cycle regulation. In mammalian cells, CDK1, with its binding partners cyclin A2 and B1, alone can drive the cell cycle. Cyclin-CDK complexes of earlier cell-cycle phase can help to activate cyclin-CDK complexes in later phase.

The same CDK may form complexes with different cyclins to regulate different phases of the cell cycle. For example, CDK2 may form a complex with cyclin D or E to regulate G1 phase; form a complex with cyclin A or E to regulate S phase; and form a complex with cyclin A to regulate G2 phase. Meanwhile, CDK4 and CDK6 can form complexes with cyclins D1, D2, and D3.

The highly homologous Cyclin-dependent kinases (CDKs) CDK4 and CDK6 in combination with Cyclin D are key regulators of the transition through the restriction point R between the G1 (growth) and S (DNA replication) phases of the cell cycle. CDK4/6 exert their effects via phosphorylation of the retinoblastoma protein (pRb). Once phosphorylated, pRb loses its inhibitory effect on the transcription of genes promoting entry into S phase.

By contrast, specific inhibition of CDK4/6 kinase activity by the endogenous protein modulator $p16^{INK4}$ or by small molecule inhibitors results in hypophosphorylated pRb and arrest of the cells at the G1 restriction point. As the primary mechanism of regulating the G1 restriction point, the pathway regulated by these kinases is altered in a broad spectrum of human tumors, and thus inhibition of CDK4/CDK6 in these tumors has therapeutic benefit by preventing cell division.

There remains a need to provide CDK4/6 inhibitors which can be used in the treatment of cell proliferative disorders such as cancer.

SUMMARY OF THE INVENTION

Described herein are compounds that inhibit the activity of a cyclin-dependent kinase (CDK), e.g., CDK2, CDK4, and/or CDK6, and pharmaceutically acceptable salts, or stereoisomers thereof.

In one aspect, the invention provides a compound represented by the following structural formula:

(Compound A)

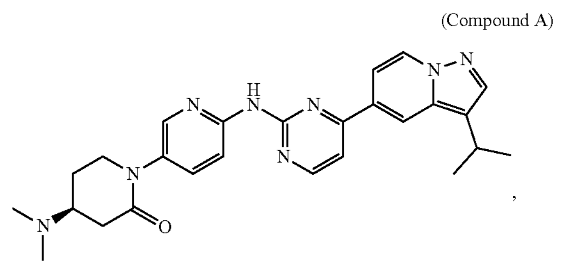 [SMILES: CC(C)c1cnn2ccc(-c3ccnc(Nc4ccc(N5CC[C@H](N(C)C)CC5=O)cn4)n3)cc12]

, or a pharmaceutically acceptable salt thereof. It is discovered that Compound A not only actively inhibits CDK2, CDK4 and CDK6, but also demonstrates strong anti-proliferation activities.

In another aspect, the invention provides a compound represented by the following structural formula:

(Compound B)

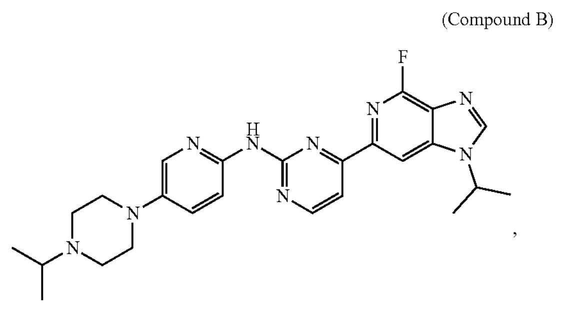 [SMILES: CC(C)N1CCN(c2ccc(Nc3nccc(-c4cc5c(ncn5C(C)C)c(F)n4)n3)nc2)CC1]

, or a pharmaceutically acceptable salt thereof. It is discovered that Compound B selectively inhibit CDK4 but also has excellent brain penetration.

Also provided are pharmaceutical compositions comprising the compounds disclosed herein, or a pharmaceutically acceptable salt, or a stereoisomer thereof and a pharmaceutically acceptable carrier.

The present disclosure further provides a method of treating cancer in a subject in need thereof, comprising administering to the subject an effective amount of (1) a compound disclosed herein or a pharmaceutically acceptable salt, or a stereoisomer thereof; or (2) a pharmaceutically acceptable composition comprising the compound disclosed herein or a pharmaceutically acceptable salt, or a stereoisomer thereof, and a pharmaceutically acceptable carrier. In certain embodiments, the cancer is selected from the group consisting of colorectal cancer, breast cancer (such as hormone receptor positive, HER2/neu negative advanced or metastatic breast cancer in postmenopausal women), lung cancer, prostate cancer, glioblastoma, mantel cell lymphoma, chronic myeloid leukemia and acute myeloid leukemia.

In certain embodiments of the methods of the invention, the cancer can be treated by inhibiting the activity of a cyclin-dependent kinase (CDK), e.g., CDK2, CDK4, and/or CDK6.

In certain embodiments of the methods of the invention, the cancer is carcinoma of the bladder, breast, colon, kidney, epidermis, liver, lung, oesophagus, gall bladder, ovary, pancreas, stomach, cervix, thyroid, nose, head and neck, prostate, or skin; a hematopoietic tumor of lymphoid lineage; a hematopoietic tumor of myeloid lineage; thyroid follicular cancer; a tumor of mesenchymal origin; a tumor of the central or peripheral nervous system; melanoma; seminoma; teratocarcinoma; osteosarcoma; xeroderma pigmentosum; keratoctanthoma; thyroid follicular cancer; or Kaposi's sarcoma.

In certain embodiments of the methods of the invention, the compounds disclosed herein are administered with any one of a second therapeutic agent as described herein that also treats the same cancer.

The present disclosure also provides a use of the compound disclosed herein or a pharmaceutically acceptable salt, or a stereoisomer thereof or a pharmaceutical composition comprising the same in any of the methods of the invention described above. In one embodiment, provided is the compound disclosed herein or a pharmaceutically acceptable salt, or a stereoisomer thereof or a pharmaceutical composition comprising the same for use in any of the method of the invention described above. In another embodiment, provided is use of the compound disclosed herein or a pharmaceutically acceptable salt, or a stereoisomer thereof or a pharmaceutical composition comprising the same for the manufacture of a medicament for any of the method of the invention described.

DETAILED DESCRIPTION OF THE INVENTION

1. Overview

The present invention provides a compound of the present invention or a pharmaceutically acceptable salt thereof for use in therapy, such as cancer therapy.

The present also invention provides a pharmaceutical formulation comprising a compound of the present invention or a pharmaceutically acceptable salt thereof, and a pharmaceutically acceptable carrier, diluent, or excipient.

The present invention provides a compound of the present invention or a pharmaceutically acceptable salt thereof for use in the treatment of cancer. In particular, those cancers may be any of the cancers described herein below, such as colorectal cancer, breast cancer (including $ER^+HER2^-$ advanced or metastatic or recurrent breast cancer is in an adult woman, or a postmenopausal woman), lung cancer, especially non-small cell lung cancer (NSCLC), prostate cancer, glioblastoma, mantel cell lymphoma (MCL), chronic myeloid leukemia (CML) and acute myeloid leukemia (AML).

This invention further provides a method of treating cancer selected from the group consisting of colorectal cancer, breast cancer (including $ER^+HER2^-$ advanced or metastatic or recurrent breast cancer is in an adult woman, or a postmenopausal woman), lung cancer, especially non-small cell lung cancer (NSCLC), prostate cancer, glioblastoma, mantel cell lymphoma, chronic myeloid leukemia and acute myeloid leukemia in a mammal comprising administering to a mammal in need of such treatment an effective amount of a compound of the present invention or a pharmaceutically acceptable salt thereof.

Additionally, this invention provides the use of a compound of the present invention or a pharmaceutically acceptable salt thereof for the manufacture of a medicament for the treatment of cancer. In particular those cancers are selected from the group consisting of colorectal cancer, breast cancer (including $ER^+HER2^-$ advanced or metastatic or recurrent breast cancer is in an adult woman, or a postmenopausal woman), lung cancer, especially non-small cell lung cancer (NSCLC), prostate cancer, glioblastoma, mantel cell lymphoma, chronic myeloid leukemia and acute myeloid leukemia.

Furthermore, this invention provides a pharmaceutical formulation for use in therapy comprising a compound of the present invention or a pharmaceutically acceptable salt thereof and a pharmaceutically acceptable carrier, diluent, or excipient. The invention also provides a pharmaceutical formulation for treating colorectal cancer, breast cancer (including $ER^+HER2^-$ advanced or metastatic or recurrent breast cancer is in an adult woman, or a postmenopausal woman), lung cancer, especially non-small cell lung cancer (NSCLC), prostate cancer, glioblastoma, mantel cell lymphoma, chronic myeloid leukemia and acute myeloid leukemia comprising a compound of the present invention or a pharmaceutically acceptable salt thereof and a pharmaceutically acceptable carrier, diluent, or excipient.

Treatable disease indications and potential second therapeutic agent useful for combination therapy are described in further detail in the sections below.

It should be understood that any embodiment described herein, including those described only in one of the sections below or only in the examples, may be combined with any one or more additional embodiments of the invention, unless expressly disclaimed or otherwise improper/inapplicable.

2. Definitions

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer.

Enantiomeric and diastereomeric mixtures can be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and diastereomers can also be obtained from diastereomerically- or enantiomerically-pure intermediates, reagents, and catalysts by well-known asymmetric synthetic methods. See, for example, Jacques et al., Enantiomers, Racemates and Resolutions (Wiley Interscience, New York, 1981); Wilen et al., Tetrahedron 33:2725 (1977); Eliel, E. L. Stereochemistry of Carbon Compounds (McGraw-Hill, NY, 1962); and Wilen, S. H. Tables of Resolving Agents and Optical Resolutions p. 268 (E. L. Eliel, Ed., Univ. of Notre Dame Press, Notre Dame, IN 1972).

When a compound is designated by a name or structure that indicates a single enantiomer, unless indicated otherwise, the compound is at least 60%, 70%, 80%, 90%, 99% or 99.9% optically pure (also referred to as "enantiomerically pure"). Optical purity is the weight in the mixture of the named or depicted enantiomer divided by the total weight in the mixture of both enantiomers.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers are included. It is to be further understood that the stereoisomeric purity of the named or depicted stereoisomers at least 60%, 70%, 80%, 90%, 99% or 99.9% by weight. The stereoisomeric purity in this case is determined by dividing the total weight in the mixture of the stereoisomers encompassed by the name or structure by the total weight in the mixture of all of the stereoisomers.

When a geometric isomer is depicted by name or structure, it is to be understood that the geometric isomeric purity of the named or depicted geometric isomer is at least 60%, 70%, 80%, 90%, 99% or 99.9% pure by weight. Geometric isomeric purity is determined by dividing the weight of the named or depicted geometric isomer in the mixture by the total weight of both geometric isomers in the mixture.

Racemic mixture means 50% of one enantiomer and 50% of is corresponding enantiomer. The invention encompasses all enantiomerically-pure, enantiomerically-enriched, diastereomerically pure, diastereomerically enriched, and racemic mixtures, and diastereomeric mixtures of the compounds of the invention.

The compounds described herein may also include all isotopes of atoms occurring in the intermediates or final compounds. Isotopes include those atoms having the same atomic number but different mass numbers. For example, isotopes of hydrogen include tritium and deuterium.

It will be recognized that some variation of natural isotopic abundance occurs in a synthesized compound depending upon the origin of chemical materials used in the synthesis. Thus, a preparation of the compound disclosed herein will inherently contain small amounts of deuterated isotopologues. The concentration of naturally abundant stable hydrogen and carbon isotopes, notwithstanding this variation, is small and immaterial as compared to the degree of stable isotopic substitution of compounds of this invention. See, for instance, Wada, E et al., Seikagaku, 1994, 66:15; Gannes, L Z et al., Comp Biochem Physiol Mol Integr Physiol, 1998, 119:725.

The compounds described herein may exist in various tautomeric forms. The term "tautomers" or "tautomeric" refers to two or more interconvertible compounds/substituents resulting from at least one formal migration of a hydrogen atom and at least one change in valency (e.g., a single bond to a double bond, a triple bond to a single bond, or vice versa). Exemplary tautomerizations include keto-to-enol, amide-to-imide, lactam-to-lactim, enamine-to-imine, and enamine-to-(a different enamine) tautomerizations. The present teachings encompass compounds in the form of tautomers, which includes forms not depicted structurally. All such isomeric forms of such compounds are expressly included. If a tautomer of a compound is aromatic, this compound is aromatic. Similarly, if a tautomer of a compound is a heteroaryl, this compound is heteroaryl.

In certain instances tautomeric forms of the disclosed compounds exist, such as the tautomeric structures shown below:

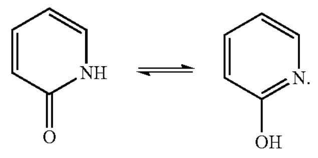 [SMILES: O=c1cccc[nH]1 ; Oc1ccccn1]

It is to be understood that when a compound herein is represented by a structural formula or designated by a chemical name herein, all other tautomeric forms which may exist for the compound are encompassed by the structural formula.

The compounds of this invention can exist in free form for treatment, or where appropriate, as a pharmaceutically acceptable salt form.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art, for example, Berge et al. describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}\ alkyl)_4^-$ salts. Representative alkali or alkaline earth metal salts include sodium, lithium, potassium, calcium, magnesium, and the like. Further pharmaceutically acceptable salts include, when appropriate, ammonium, quaternary ammonium, and amine cations formed using counterions such as halide, hydroxide, carboxylate, sulfate, phosphate, nitrate, lower alkyl sulfonate, and aryl sulfonate.

Such pharmaceutically acceptable acid addition salts and common methodology for preparing them are well known in the art. See, e.g., Stahl et al., HANDBOOK OF PHARMACEUTICAL SALTS: PROPERTIES, SELECTION AND USE, (VCHA/Wiley-VCH, 2002); Bighley et al., in "*Encyclopedia of Pharmaceutical Technology*." Eds. Swarbrick and Boylan, Vol. 13, Marcel Dekker, Inc., New York, Basel, Hong Kong 1995, pp. 453-499; Berge et al., "Pharmaceutical Salts," *Journal of Pharmaceutical Sciences,* 66(1): 1977.

The terms "composition" and "formulation" are used interchangeably.

A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

The term "administer," "administering," or "administration" refers to methods introducing a compound of the invention, or a composition thereof, in or on a subject. These methods include, but are not limited to, intraarticular (in the joints), intravenous, intramuscular, intratumoral, intradermal, intraperitoneal, subcutaneous, orally, topically, intrathecally, inhalationally, transdermally, rectally, and the like. Administration techniques that can be employed with the agents and methods described herein are found in e.g., Goodman and Gilman, *The Pharmacological Basis of Therapeutics*, current ed.; Pergamon; and Remington's, *Pharmaceutical Sciences* (current edition), Mack Publishing Co., Easton, Pa.

The terms "treatment," "treat," and "treating" refer to reversing, alleviating, or inhibiting the progress of a disease described herein. In some embodiments, treatment may be administered after one or more signs or symptoms of the disease have developed or have been observed (i.e., therapeutic treatment). In other embodiments, treatment may be administered in the absence of signs or symptoms of the disease. For example, treatment may be administered to a susceptible subject prior to the onset of symptoms (i.e., prophylactic treatment) (e.g., in light of a history of symptoms and/or in light of exposure to a pathogen). Treatment may also be continued after symptoms have resolved, for example, to delay or prevent recurrence.

The terms "condition," "disease," and "disorder" are used interchangeably.

Generally, an effective amount of a compound taught herein varies depending upon various factors, such as the given drug or compound, the pharmaceutical formulation, the route of administration, the type of disease or disorder, the identity of the subject or host being treated, and the like, but can nevertheless be routinely determined by one skilled in the art. An effective amount of a compound of the present teachings may be readily determined by one of ordinary skill by routine methods known in the art.

The term "an effective amount" means an amount when administered to the subject which results in beneficial or desired results, including clinical results, e.g., inhibits, suppresses or reduces the symptoms of the condition being treated in the subject as compared to a control. For example, an effective amount can be given in unit dosage form (e.g., from 1 mg to about 50 g per day, e.g., from 1 mg to about 5 grams per day).

A "therapeutically effective amount" is that amount effective for detectable killing or inhibition of the growth or spread of cancer cells; the size or number of tumors; or other measure of the level, stage, progression or severity of the cancer. The exact amount required will vary from subject to subject, depending on the species, age, and general condition of the subject, the severity of the disease, the particular anticancer agent, its mode of administration, combination treatment with other therapies, and the like.

The general chemical terms used in the formulae above have their usual meanings.

As used herein, "h" refers to hour or hours, "min" refers to minutes or minutes, "Cdk" or "CDK" refers to cyclin dependent kinase, "pRb" refers to retinoblastoma protein, "MCL" refers to mantle cell lymphoma, "AML" refers to acute myeloid leukemia, "CML" refers to chronic myeloid leukemia, "Boc" refers to N-tert-butoxycarbonyl, "EA" refers to ethyl acetate, "DCM" refers to dichloromethane, "DMSO" refers to dimethylsulfoxide, "DMA" refers to dimethylacetamide, "THF" refers to tetrahydrofuran, "MtBE" refers to methyl tert-butyl ether, "TEA" refers to triethylamine, "FBS" refers to fetal bovine serum, "PBS" refers to phosphate buffered saline, "BSA" refers to bovine serum albumin, "RT" refers to room temperature, "mpk" means milligrams per kilogram, "po" refers to per os (oral), "qd" means once daily dosing, "HPLC" means high pressure liquid chromatography, "q2d" means a single dose every 2 days, "q2d×10" means a single dose every 2 days times 10, "VSMC" refers to vascular smooth muscle cell and "XRD" refers to X-ray diffraction.

3. Compounds

Another aspect of the present disclosure relates to labeled compounds of the invention (radio-labeled, fluorescent-labeled, etc.) that would be useful not only in imaging techniques but also in assays, both in vitro and in vivo, for localizing and quantitating CDK in tissue samples, including human, and for identifying CDK ligands by inhibition binding of a labeled compound. Accordingly, the present disclosure includes such labeled compounds.

The present disclosure further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^2H$ (also written as D for deuterium), $^3H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radio-labeled compounds will depend on the specific application of that radio-labeled compound.

The present invention can further include synthetic methods for incorporating radio-isotopes into compounds of the invention. Synthetic methods for incorporating radio-isotopes into organic compounds are well known in the art, and an ordinary skill in the art will readily recognize the methods applicable for the compounds of invention.

A labeled compound of the invention can be used in a screening assay to identify/evaluate compounds. For example, a newly synthesized or identified compound (i.e., test compound) which is labeled can be evaluated for its ability to bind a CDK by monitoring its concentration variation when contacting with the CDK, through tracking of the labeling. For example, a test compound (labeled) can be evaluated for its ability to reduce binding of another compound which is known to bind to a CDK (i.e., standard compound). Accordingly, the ability of a test compound to compete with the standard compound for binding to the CDK directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

In one embodiment, the compound or a pharmaceutically acceptable salt, or a stereoisomer thereof, wherein one or more hydrogen atoms are replaced by deuterium.

4. Treatable Diseases and Method of Treatment

Certain compounds of the present invention are selective inhibitors of CDK2, CDK4, and/or CDK6, and are therefore useful in the treatment of a disease or disorder characterised by abnormal cell proliferation that can be inhibited by a reduced activity of CDK-cyclin complexes encompassing CDK2, CDK4, and/or CDK6.

In certain embodiments, compounds of the invention selectively inhibit CDK4/6 over CDK2, with a ratio of $IC_{50}$ values for the latter (CDK2) against the former (CDK4/6) of at least about 10, 20, 50, 100, 200, 300, 400, 500, 800, 1,000, 2,000 or more.

In certain embodiments, compounds of the invention selectively inhibit CDK4 over CDK6, with a ratio of $IC_{50}$ values for the latter (CDK6) against the former (CDK4) of at least about 2, 3, 4, 5, 6, 7, 8, 9, 10, 15, 20, 50 or more.

In certain embodiments, compounds of the invention selectively inhibit CDK2 over CDK4, with a ratio of $IC_{50}$ values for the latter (CDK4) against the former (CDK2) of at least about 2, 5, 10, 15, 20, 40, 50, 60, 80, 100 or more.

In certain embodiments, compounds of the invention inhibits CDK2/4/6 with similar $IC_{50}$ values, e.g., $IC_{50}$ values within 10-, 5-, 3-, or 2-fold. Such compounds of the invention are useful for treating cancers with cyclin D1 or E1 or E2 amplification or enhanced expression.

CDK2 is the catalytic subunit of the CDK-cyclin complex whose activity is restricted to the G1-S phase of the cell cycle, where cells make proteins necessary for mitosis and replicate their DNA. CDK2 is complexed with cyclin E or A. Cyclin E binds G1 phase CDK2, which is required for G1 to S phase transition. On the other hand, CDK2 binding with Cyclin A is required to progress through the S phase.

Although CDK2 is mostly dispensable in the cell cycle of normally functioning cells, it is critical to the abnormal growth processes of cancer cells. Overexpression of cyclin E occurs in many tumor cells, causing the cells to become dependent on CDK2 and cyclin E. Abnormal cyclin E activity is observed in breast, lung, colorectal, gastric, and bone cancers, as well as in leukemia and lymphoma. Likewise, abnormal expression of cyclin A2 is associated with chromosomal instability and tumor proliferation, while inhibition leads to decreased tumor growth. Therefore, CDK2 and its cyclin binding partners represent possible therapeutic targets for new cancer therapeutics. Pre-clinical models have shown preliminary success in limiting tumor growth, and have also been observed to reduce side effects of current chemotherapy drugs.

For example, Caldon et al. (*Mol Cancer Ther* 11(7):1488-1499, 2012) reported that Cyclin E2 is included in several gene signatures that predict disease progression in either tamoxifen-resistant or metastatic breast cancer, and high expression of CycE2 was characteristic of the luminal B and HER2 subtypes of breast cancer and was strongly predictive of shorter distant metastasis-free survival following endocrine therapy. Further, tamoxifen-resistant (MCF-7 TAMR) breast cancer cells overexpressed cyclin E2; and expression of either cyclin E1 or E2 in T-47D breast cancer cells conferred acute antiestrogen resistance, suggesting that cyclin E overexpression contributes to the antiestrogen resistance of tamoxifen-resistant cells. Proliferation of tamoxifen-resistant cells was inhibited by RNAi-mediated knockdown of cyclin E1, cyclin E2, or CDK2. Besides, ectopic expression of cyclin E1 or E2 also reduced sensitivity to CDK4, but not CDK2, inhibition. Furthermore, CDK2 inhibition of E-cyclin overexpressing cells and tamoxifen-resistant cells restored sensitivity to tamoxifen or CDK4 inhibition.

These data demonstrate that Cyclin E2 overexpression is a potential mechanism of resistance to both endocrine therapy and CDK4 inhibition, and CDK2 inhibitors may in turn ovecome such resistance, and may be beneficial as a component of combination therapies in endocrine-resistant disease as they effectively inhibit cyclin E1 and E2 overexpressing cells and enhance the efficacy of other therapeutics. Likewise, the subject compounds with potent inhibitory activities against both CDK2 and CDK4 are expected to be effective against cancer cells that are both non-resistant and resistant to endocrine therapy or CDK4 inhibition.

Thus in certain embodiments, the compounds of the invention may have potent inhibitory effects against both CDK2 and CDK4 (e.g., independently <10 nM, <5 nM, <1 nM level of $IC_{50}$ values), and thus are effective to treat tamoxifen-resistant or metastatic breast cancers, such as tamoxifen-resistant or metastatic breast cancers with CycE overexpression.

$IC_{50}$ values of the compounds of the invention against CDK2/4/6 can be measured using, for example, the methods described in Examples 1-3 (incorporated herein by reference).

In particular, the compounds of the present invention are useful in the treatment of cancer. In other embodiments, the compounds of the present invention are useful in the treatment of chronic inflammation diseases such as arthritis and cystic fibrosis.

Thus in one aspect, the present invention provides a method of treating cancer, in particular the cancers described herein, in a mammal, comprising administering to a mammal in need of such treatment an effective amount of a compound of the present invention.

In a related aspect, the invention is directed to a use of a compound of the present invention in the manufacture of a medicament for treating cancer, in particular, the cancers described herein.

In another related aspect, the compounds of the present invention can be used in the manufacture of a medicament for the treatment of cancer, in particular, the cancers described herein.

In another related aspect, the invention provides a compound of the present invention for use in treating cancer, in particular, the cancers described herein.

According to any of the above related aspects of the invention, CDK4 and CDK6 may modulate their effects on the cell cycle partly through pRb phosphorylation. Thus, certain compounds of the present invention may inhibit pRb phosphorylation through inhibiting CDK4/6 activity, and thus inhibiting cell proliferation and/or tumor growth, in any cancer type where the cells are proliferating and contain a functional, intact Rb1 gene that encodes pRb.

Thus in certain embodiments, the compounds of the invention are useful in the treatment of $pRb^+$ cancers, such as colorectal cancer, breast cancer, lung cancer, prostate cancer, chronic myeloid leukemia, acute myeloid leukemia (Fry et al., *Mol. Cancer Ther.* 3(11):1427, 2004), mantel cell lymphoma (Marzec et al., *Blood* 108(5):1744, 2006), ovarian cancer (Kim et al., *Cancer Research* 54:605, 1994), pancreatic cancer (Schutte et al., *Cancer Research* 57:3126, 1997), malignant melanoma and metastatic malignant melanoma (Maelandsmo et al., *British Journal of Cancer* 73:909, 1996) in mammals. The compounds of the invention are also expected to be useful in the treatment of rhabdomyosarcoma (Saab et al., *Mol. Cancer. Ther.* 5(5):1299, 2006) and multiple myeloma (Baughn et al., *Cancer Res.* 66(15):7661, 2006), including relapsed refractory multiple myeloma, in mammals (e.g., human).

Meanwhile, Zhang et al. (*Nature* dx.doi.org/10.1038/nature25015, 2017) reported that inhibition of CDK4/6 in vivo may lead to decreased phosphorylation and therefore increased degradation of Cullin $3^{SPOP}$ E3 ligase (by APC/$C^{Cdh1}$), which in turn leads to increased PD-L1 levels on tumor cell surface, and reduced numbers of tumor-infiltrating lymphocytes (TILs) in mouse tumors and in primary human prostate cancer specimens. In other words, inhibition of CDK4/6 in vivo elevates PD-L1 protein levels, and contributes to increased resistance to immune checkpoint therapy targeting PD-1 (programmed cell death protein 1) and PD-L1 (ligand for PD-1). On the other hand, combining CDK4/6 inhibitor treatment with anti-PD-1 immunotherapy enhances tumor regression, and dramatically improves overall survival rates in mouse tumor models.

Thus in certain embodiments, the compounds of the invention can be used in combination with PD-1/PD-L1 immune checkpoint inhibitors to enhance therapeutic efficacy for human cancers.

PD-1 and PD-L1 inhibitors that can be used with the compounds of the invention are known in the art. PD-1 inhibitors include monoclonal antibodies or antigen binding fragment thereof specific for PD-1. Exemplary PD-1 inhibitors include Pembrolizumab (Keytruda), Nivolumab (Opdivo), and Cemiplimab (Libtayo). PD-L1 inhibitors include monoclonal antibodies or antigen binding fragment thereof specific for PD-L1. Exemplary PD-L1 inhibitors include Atezolizumab (Tecentriq), Avelumab (Bavencio), and Durvalumab (Imfinzi).

Additional immune checkpoint inhibitor that may be used with the compounds of the invention for enhancing therapeutic efficacy for human cancers include monoclonal antibodies or antigen binding fragments thereof specific for CTLA-4 such as Ipilimumab (Yervoy).

Further immune checkpoint inhibitor that may be used with the compounds of the invention for enhancing therapeutic efficacy for human cancers include bispecific monoclonal antibodies or antigen binding fragments thereof specific for PD-1 and PD-L1, or combination of monoclonal antibodies or antigen binding fragments thereof specific for PD-1 and PD-L1, or PD-1 and CTLA-4, etc.

In certain embodiments, the compounds of the invention can be used in combination with Tyr kinase inhibitor, e.g., receptor Tyr kinase (RTK) inhibitors, to enhance therapeutic efficacy for human cancers. Exemplary Tyr kinase inhibitors include ALK inhibitors (such as Crizotinib, Ceritinib, Alectinib, Brigatinib), Bcr-Abl inhibitors (such as Bosutinib, Dasatinib, Imatinib, Nilotinib, Ponatinib), BTK inhibitor (such as Ibrutinib), c-Met inhibitor (such as Crizotinib, Cabozantinib), EGFR inhibitor (such as Gefitinib, Erlotinib, Lapatinib, Vandetanib, Afatinib, Osimertinib), JAK inhibitor (such as Ruxolitinib, Tofacitinib), MEK1/2 inhibitor (such as Trametinib), PDGFR inhibitor (such as Axitinib, Gefitinib, Imatinib, Lenvatinib, Nintedanib, Pazopanib, Regorafenib, Sorafenib, Sunitinib), RET inhibitor (such as Vandetanib), Src family kinase inhibitors (such as Bosutinib, Dasatinib, Ponatinib, Vandetanib), and VEGFR family inhibitors (such as Axitinib, Lenvatinib, Nintedanib, Regorafenib, Pazopanib, Sorafenib, Sunitinib).

Additional suitable kinase inhibitors that can be used in combination with the subject compounds, as well as the treatable cancer indications, are described in Bhullar et al., *Molecular Cancer* 17:48, 2018 (incorporated herein by reference in its entirety).

Further additional RTK inhibitors include monoclonal antibodies and antigen-binding fragments thereof, including the anti-EGFR mAB such as cetuximab (effective in treating, e.g., lung, colorectal, and head and neck cancer), and the anti-HER2 mAb such as trastuzumab (effective to treat, for example, breast cancer).

In certain embodiments, the compounds of the invention can be used in combination with an antagonist of hormonal receptor signaling, such as the ones described before for breast cancer treatment.

Cancers treatable with the compounds of the invention include: Non-Hodgkin's lymphoma; malignant mesothelioma; non-small cell lung cancer; cholangiocarcinoma; soft tissue sarcoma; glioblastoma; (recurrent) brain tumor; brain metastases secondary to hormone receptor positive breast cancer, non-small cell lung cancer, melanoma (including melanoma positive for cyclin D1 expression); (recurrent or persistent) endometrial cancer; (recurrent or metastatic) Head and Neck Squamous Cell Carcinoma (HNSCC); hepatocellular carcinoma; esophageal squamous cell carcinoma (SCC); esophageal adenocarcinoma (ADC); renal cell carcinoma, and urothelial cancer.

In certain embodiments, the treatable cancers include: carcinoma of the bladder, breast, colon, kidney, epidermis, liver, lung (including SCLC and NSCLC), esophagus, gall bladder, ovary, pancreas, stomach, cervix, thyroid, nose, head and neck, prostate, or skin; a hematopoietic tumor of lymphoid lineage; a hematopoietic tumor of myeloid lineage; thyroid follicular cancer; a tumor of mesenchymal origin; a tumor of the central or peripheral nervous system; melanoma; familial melanoma; seminoma; teratocarcinoma; osteosarcoma; xeroderma pigmentosum; keratoctanthoma; thyroid follicular cancer; Kaposi's sarcoma, squamous cancer, sarcoma; or a tumor of mesenchymal origin.

In certain embodiments, the hematopoietic tumor of lymphoid lineage is leukemia, acute lymphocytic leukemia, chronic lymphocytic leukemia, B-cell lymphoma, T-cell lymphoma, multiple myeloma, Hodgkin's lymphoma, non-Hodgkin's lymphoma, hairy cell lymphoma, or Burkett's lymphoma.

In certain embodiments, the tumor of the central or peripheral nervous system is astrocytoma, neuroblastoma, glioma or schwannoma.

In certain embodiments, the cancer is small cell lung cancer, non-small cell lung cancer, pancreatic cancer, breast cancer, glioblastoma multiforme, T cell ALL and mantle cell lymphoma.

In certain embodiments, the cancer is selected from the group consisting of: colorectal cancer, mantel cell lymphoma, breast cancer (including advanced or metastatic or recurrent breast cancer), pancreatic cancer, ovarian cancer, glioblastoma, acute myeloid leukemia, and lung cancer, especially NSCLC.

In certain embodiments, the cancer is NSCLC, pancreatic cancer, ovarian cancer or metastatic breast cancer, and the treatment comprising administering to a mammal in need thereof a therapeutically effective combination of a compound of the present invention and gemcitabine HCl.

In certain embodiments, the cancer is NSCLC, pancreatic cancer, ovarian cancer or metastatic breast cancer, wherein the medicament comprising the compound of the present invention also comprises gemcitabine HCl, or is to be administered simultaneously, separately or sequentially with gemcitabine HCl.

In certain embodiments, the compounds of the present invention can be used in combination with other agents for the treatment of NSCLC, pancreatic cancer, ovarian cancer and metastatic breast cancer. For example, the compound of the present invention may be used in simultaneous, separate or sequential combination with gemcitabine HCl in the treatment of NSCLC, pancreatic cancer, ovarian cancer or metastatic breast cancer.

In certain embodiments, the cancer is selected from the group consisting of colorectal cancer, glioblastoma, acute myeloid leukemia and lung cancer.

In certain embodiments, the cancer is glioblastoma or astrocytoma, and the treatment utilizes a therapeutically effective combination of a compound of the invention and temozolomide. The compound of the invention may be administered simultaneously, separately or sequentially with temozolomide.

Breast Cancer Treatment

In certain embodiments, the compounds of the invention can be used to treat breast cancer.

Breast cancer presents a significant health burden worldwide, and it alone accounted for ~7% of all US cancer-related deaths in 2016. Of all breast cancers, about 75% are diagnosed as hormone receptor-positive ($HR^+$) breast cancer, which expresses the estrogen receptor (ER) and/or the progesterone receptor (PgR), and is typically dependent on the ER signaling pathway for growth and survival. That is, the $HR^+$ breast cancers harness the biological functions of the ER pathway to promote breast cancer growth, development, and progression. Meanwhile, the reliance of $HR^+$ breast cancer on ER signaling made such breast cancer a therapeutic target for endocrine therapy agents that target the estrogen signaling pathway, such as aromatase inhibitors (AIs; including letrozole, anastrozole, and exemestane), selective ER modulators (tamoxifen), and selective ER down-regulators (fulvestrant), etc.

Although endocrine therapy makes up the treatment backbone for $HR^+$ breast cancer, the efficacy of endocrine therapy is limited by high rates of both pre-existing de novo resistance, and resistance acquired during treatment, due to the presence of alternative survival or "escape" pathway. The ER pathway and many of the known escape pathways act through the cyclin D-CDK4/6-inhibitor of CDK4 (INK4)-retinoblastoma (Rb) pathway to promote tumor growth. As such, targeting both the ER and the cyclin D-CDK4/6-INK4-Rb pathways in combination usually lead to a more extensive inhibition of tumor growth and prevent the activation of escape pathways, precluding the development of endocrine therapy resistance. See Sammons et al., *Current Cancer Drug Targets* 17:637-649, 2017.

Thus in certain embodiments, the breast cancer is a pRb+ breast cancer. In certain embodiments, the breast cancer is a hormone receptor (HR)-positive (e.g., estrogen receptor positive ($ER^+$), progesterone receptor positive ($PR^+$), or $ER^+PR^+$), HER2/neu-negative cancer, including $HR^+HER2^-$ or $ER^+HER2^-$, advanced or metastatic or recurrent breast cancer. In certain embodiments, the $HR^+HER2^-$ or $ER^+HER2^-$ advanced or metastatic or recurrent breast cancer is in an adult woman, or a postmenopausal woman.

In certain embodiments, the compounds of the invention is either used alone, or used with an aromatase inhibitor (that inhibits estrogen production), to treat HR-positive, HER2-negative advanced or metastatic or recurrent breast cancer. In certain embodiments, the aromatase inhibitor temporarily inactivate aromatase (such as anastrozole (ARIMIDEX®) and letrozole (FEMARA®)). In certain embodiments, the aromatase inhibitor permanently inactivate aromatase (such as exemestane (AROMASIN®)).

In certain embodiments, the compound(s) of the invention is used with a compound that interferes with estrogen's ability to stimulate the growth of breast cancer cells, such as a Selective Estrogen Receptor Modulator (SERM) that binds to the estrogen receptor to prevent estrogen binding, such as tamoxifen (NOLVADEX®) and toremifene (FARESTON®). Tamoxifen has been used for more than 30 years to treat $HR^+$ breast cancer.

In certain embodiments, the compound(s) of the invention is used with a pure antiestrogen with no estrogen agonist activity, such as fulvestrant (FASLODEX®).

In certain embodiments, the HR-positive, HER2-negative advanced or metastatic or recurrent breast cancer is in a postmenopausal woman. In certain embodiments, the HR-positive, HER2-negative advanced or metastatic or recurrent breast cancer has progressed after taking therapy that alters a patient's hormones (e.g., estrogen and/or progesterone), or has worsened after treatment with another hormone therapy.

In certain embodiments, the compound(s) of the invention is used in a patient undergoing ovarian ablation, or has received ovarian ablation. In certain embodiments, the ovarian ablation is through oophorectomy or radiation treatment.

In certain embodiments, the compound(s) of the invention is used with a compound that temporarily suppresses ovarian function (e.g., estrogen and/or progesterone production). Such compound includes gonadotropin-releasing hormone (GnRH) agonists or luteinizing hormone-releasing hormone (LH-RH) agonists, including goserelin (ZOLADEX®) and leuprolide (LUPRON®).

In certain embodiments, the compound(s) of the invention is used with a compound that inhibits CYP3A4, such as ritonavir, indinavir, nelfinavir, saquinavir, clarithromycin, telithromycin, chloramphenicol, ketoconazole, itraconazole, posaconazole, voriconazole, nefazodone, cobicistat, amiodarone, aprepitant, verapamil, diltiazem, erythromycin, fluconazole, miconazole, bergamottin, cimetidine, ciprofloxacin, cyclosporine, donedarone, fluvoxamine, imatinib, Valerian, buprenorphine, cafestol, cilostazol, fosaprepitant, gabapentin, lomitapide, orphenadrine, ranitidine, ranolazine, tacrolimus, ticagrelor, valproic acid, amlodipine, cannabidiol, dithiocarbamate, mifepristone, norfloxacin, delavirdine, gestodene, mibefradil, star fruit, milk thistle, niacinamide, *Ginkgo biloba*, piperine, isoniazid, and quercetin.

In certain embodiments, the compound(s) of the invention is used with an inhibitor of IGF-1/IGF-2, such as a monoclonal antibody or an antigen-binding fragment thereof against IGF-1/IGF-2. Exemplary antibodies include xentuzumab, a humanized IgG1 mAb.

In certain embodiments, the compound(s) of the invention is used with a compound that inhibits PI3K. It is believed that inhibition of PI3K reduces the levels of cyclin D1 and other G1-S cyclins, abolishes pRb phosphorylation, and inhibits activation of S-phase transcriptional programs. Representative PI3K inhibitors for use with the compounds of the invention includes idelalisib, copanlisib, duvelisib, taselisib, perifosine, buparlisib, alpelisib, umbralisib, copanlisib, dactolisib, and voxtalisib.

In certain embodiments, the mammal to be treated is a human, such as an adult woman having breast cancer (e.g., postmanupausal woman or adult woman having hormone receptor (HR)-positive, human epidermal growth factor receptor 2 (HER2)-negative advanced or metastatic or recurrent breast cancer that has progressed after taking therapy that alters a patient's hormones).

Additionally, certain compounds of the present invention exhibit the advantageous property that they are able to cross the blood-brain barrier. Such compounds are therefore able to penetrate the brain and are thus useful in the treatment of primary and metastatic brain tumors where the cells are proliferating and contain a functional, intact Rb1 gene. Examples of such $pRb^+$ brain tumors include glioblastoma, as well as medulloblastoma and astrocytoma (Lee et al., Science 235:1394, 1987).

Temozolomide is a cytotoxic, DNA alkylating agent used for the treatment of brain tumors including glioblastoma and astrocytoma (Friedman et al., Clin. Cancer Res. 6(7):2585-2597, 2000) including brain metastases from melanoma, breast cancer and NSCLC (Siena et al., Annals of Oncology, doi: 10.1093/annonc/mdp343, 2009). Temozolomide interacts with DNA causing chemical modification/damage (Marchesi et al., Pharmacol. Res. 56(4):275-287, 2007). Thus, in some embodiments, the compounds of the present invention can be used in combination with temozolomide for the treatment of primary and metastatic $pRb^+$ brain tumors such as glioblastoma and astrocytoma, for example, where such metastases are derived from melanoma, breast cancer or NSCLC.

5. Pharmaceutical Compositions

The invention provides pharmaceutical compositions which comprise any one of the compounds described herein, or a pharmaceutically acceptable salt thereof, and one or more pharmaceutically acceptable carriers or excipients.

"Pharmaceutically acceptable excipient" and "pharmaceutically acceptable carrier" refer to a substance that aids the formulation and/or administration of an active agent to and/or absorption by a subject and can be included in the compositions of the present disclosure without causing a significant adverse toxicological effect on the subject. Non-limiting examples of pharmaceutically acceptable carriers and excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with or interfere with the activity of the compounds provided herein. One of ordinary skill in the art will recognize that other pharmaceutical carriers and excipients are suitable for use with disclosed compounds.

These compositions optionally further comprise one or more additional therapeutic agents. Alternatively, a compound of the invention may be administered to a patient in need thereof in combination with the administration of one or more other therapeutic regimens (e.g. Gleevec or other kinase inhibitors, interferon, bone marrow transplant, farnesyl transferase inhibitors, bisphosphonates, thalidomide, cancer vaccines, hormonal therapy, antibodies, radiation, etc). For example, additional therapeutic agents for conjoint administration or inclusion in a pharmaceutical composition with a compound of this invention may be another one or more anticancer agents.

As described herein, the compositions of the present invention comprise a compound of the invention together with a pharmaceutically acceptable carrier, which, as used herein, includes any and all solvents, diluents, or other vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Fifteenth Edition, E. W. Martin (Mack Publishing Co., Easton, Pa., 1975) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition.

6. Formulations

This invention also encompasses a class of compositions comprising the active compounds of this invention in association with one or more pharmaceutically-acceptable carriers and/or diluents and/or adjuvants (collectively referred to herein as "carrier" materials) and, if desired, other active ingredients.

In certain embodiments, the invention provides a pharmaceutical formulation for treating cancer, in particular the cancers described herein, comprising a compound of the present invention or a pharmaceutically acceptable salt thereof together with a pharmaceutically acceptable carrier.

In certain embodiments, the invention provides a pharmaceutical formulation for treating a cancer selected from the group consisting of colorectal cancer, mantel cell lymphoma, breast cancer (including $ER^+HER2^-$ advanced or metastatic or recurrent breast cancer in an adult woman, or a postmenopausal woman), glioblastoma, acute myeloid leukemia and lung cancer, especially NSCLC, comprising a compound of the present invention or a pharmaceutically acceptable salt thereof together with a pharmaceutically acceptable carrier.

In certain embodiments, the invention provides a pharmaceutical formulation for treating glioblastoma or astrocytoma, comprising a compound of the invention and temozolomide, together with a pharmaceutically acceptable carrier.

In certain embodiments, the invention also provides a pharmaceutical formulation, comprising a compound of the invention or a pharmaceutically acceptable salt thereof and temozolomide, together with a pharmaceutically acceptable carrier, diluent, or excipient.

In certain embodiments, the invention provides a pharmaceutical formulation for treating NSCLC, pancreatic cancer, ovarian cancer or metastatic breast cancer (including $ER^+HER2^-$ advanced or metastatic or recurrent breast cancer in an adult woman, or a postmenopausal woman), comprising a compound of the invention and gemcitabine HCl, together with a pharmaceutically acceptable carrier.

In certain embodiments, the invention also provides a pharmaceutical formulation, comprising a compound of the invention or a pharmaceutically acceptable salt thereof and gemcitabine HCl, together with a pharmaceutically acceptable carrier, diluent, or excipient.

The active compounds of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly, intrasternally and infusion techniques, in dosage unit formulations containing conventional pharmaceutically acceptable carriers, adjuvants, and vehicles.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension or liquid. The pharmaceutical composition is preferably made in the form of a dosage unit containing a particular amount of the active ingredient.

Examples of such dosage units are tablets or capsules. For example, a suitable daily dose for a human or other mammal may vary depending on the condition of the patient and other factors, but, once again, can be determined using routine methods.

The amount of compounds which are administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. As mentioned previously, the daily dose can be given in one administration or may be divided between 2, 3, 4 or more administrations.

For therapeutic purposes, the active compounds of this invention are ordinarily combined with one or more adjuvants, excipients or carriers appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

In the case of skin conditions, it may be preferable to apply a topical preparation of compounds of this invention to the affected area two to four times a day. Formulations suitable for topical administration include liquid or semi-liquid preparations suitable for penetration through the skin (e.g., liniments, lotions, ointments, creams, or pastes) and drops suitable for administration to the eye, ear, or nose. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

The compounds of this invention can also be administered by a transdermal device. Preferably transdermal administration will be accomplished using a patch either of the reservoir and porous membrane type or of a solid matrix variety. In either case, the active agent is delivered—continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane. The oily phase of the emulsions of this invention may be constituted from known ingredients in a known manner.

While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required.

Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients.

The active ingredients are preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable nonirritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents. Pharmaceutical compositions of this invention comprise a compound of the formulas described herein or a pharmaceutically acceptable salt thereof; an additional agent selected from a kinase inhibitory agent (small molecule, polypeptide, antibody, etc.), an immunosuppressant, an anticancer agent, an anti-viral agent, antiinflammatory agent, antifungal agent, antibiotic, or an anti-vascular hyperproliferation compound; and any pharmaceutically acceptable carrier, adjuvant or vehicle.

Alternate compositions of this invention comprise a compound of the formulae described herein or a pharmaceutically acceptable salt thereof; and a pharmaceutically acceptable carrier, adjuvant or vehicle. Such compositions may optionally comprise one or more additional therapeutic agents, including, for example, kinase inhibitory agents (small molecule, polypeptide, antibody, etc.), immunosuppressants, anti-cancer agents, anti-viral agents, antiinflammatory agents, antifungal agents, antibiotics, or anti-vascular hyperproliferation compounds.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound. Pharmaceutically acceptable carriers, adjuvants and vehicles that may be used in the pharmaceutical compositions of this invention include, but are not limited to, ion exchangers, alumina, aluminum stearate, lecithin, selfemulsifying drug delivery systems (SEDDS) such as d-atocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as u-, P-, and y-cyclodextrin, or chemically modified derivatives such as hydroxyalkylcyclodextrins, including 2 and 3-hydroxypropyl-cyclodextrins, or other solubilized derivatives may also be advantageously used to enhance delivery of compounds of the formulae described herein.

The pharmaceutical compositions may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents.

If desired, certain sweetening, flavoring and/or coloring agents may be added. The pharmaceutical compositions may comprise formulations utilizing liposome or microencapsulation techniques, various examples of which are known in the art.

The pharmaceutical compositions may be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other solubilizing or dispersing agents, examples of which are also well known in the art.

7. Treatment Kits

One aspect of the present invention relates to a kit for conveniently and effectively carrying out the methods or uses in accordance with the present invention. In general, the pharmaceutical pack or kit comprises one or more containers filled with one or more of the ingredients of the pharmaceutical compositions of the invention. Such kits are especially suited for the delivery of solid oral forms such as tablets or capsules. Such a kit preferably includes a number of unit dosages, and may also include a card having the dosages oriented in the order of their intended use. If desired, a memory aid can be provided, for example in the form of numbers, letters, or other markings or with a calendar insert, designating the days in the treatment schedule in which the dosages can be administered. Optionally associated with such container(s) can be a notice in the form prescribed by a governmental agency regulating the manufacture, use or sale of pharmaceutical products, which notice reflects approval by the agency of manufacture, use or sale for human administration.

The following representative examples contain important additional information, exemplification and guidance which can be adapted to the practice of this invention in its various embodiments and the equivalents thereof. These examples are intended to help illustrate the invention, and are not intended to, nor should they be construed to, limit its scope. Indeed, various modifications of the invention, and many further embodiments thereof, in addition to those shown and described herein, will become apparent to those skilled in the art upon review of this document, including the examples which follow and the references to the scientific and patent literature cited herein.

The contents of the cited references are incorporated herein by reference to help illustrate the state of the art.

In addition, for purposes of this invention, the chemical elements are identified in accordance with the Periodic Table of the Elements, CAS version, Handbook of Chemistry and Physics, 75$^{th}$ Ed., inside cover. Additionally, general principles of organic chemistry, as well as specific functional moieties and reactivity, are described in "Organic Chemistry," Thomas Sorrell, University Science Books, Sausalito: 1999, and "Organic Chemistry," Morrison & Boyd (3d Ed), the entire contents of both of which are incorporated herein by reference.

8. Synthesis Schemes

The compounds of Formula I can be prepared by one of ordinary skill in the art following art recognized techniques and procedures. More specifically, compounds of Formula I can be prepared as set forth in the schemes, methods, and examples set forth below. It will be recognized by one of skill in the art that the individual steps in the following schemes may be varied to provide the compounds of Formula I. The reagents and starting materials are readily available to one of ordinary skill in the art. All substituents, unless otherwise specified, are as previously defined.

EXAMPLES

Synthetic Examples

Equipment Description

1H NMR spectra were recorded on a Bruker Ascend 400 spectrometer. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), quint (quintet), m (multiplet), br (broad).

The analytical low-resolution mass spectra (MS) were recorded on Waters ACQUITY UPLC with SQ Detectors using a Waters CORTECS C18+, 2.7 μm 4.6×30 mm using a gradient elution method.

Solvent A: 0.1% formic acid (FA) in water

Solvent B: 0.1% FA in acetonitrile

5% ACN to 95% ACN in 1.0 min, hold 1.0 min,

Total 2.5 min; Flow rate: 1.8 mL/min; Column Temp 40 degree.

Intermediate

Intermediate 1

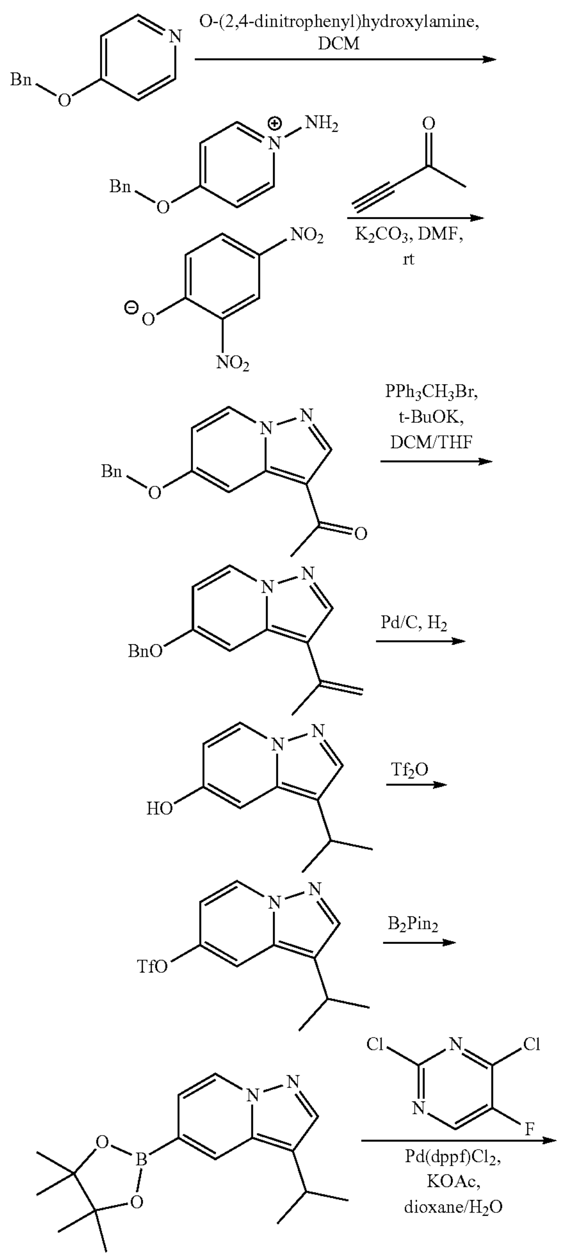

-continued

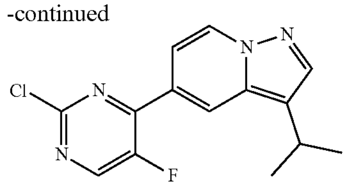

Intermediate 1

Step 1

To a solution of 4-benzyloxypyridine (185 mg, 998 μmol) in DCM (10 mL) was added amino 2,4,6-trimethylbenzenesulfonate (236 mg, 1.1 mmol) at 25° C. The reaction mixture was stirred at 25° C. for 14 h. The mixture was concentrated under reduced pressure to get crude desired product (400 mg) as colorless oil. LC-MS: m/z 202 $[M+H]^+$.

Step 2

To a solution of above product (187 mg, 487 μmol) in DMF (10 mL) was added $Cs_2CO_3$ (192 mg, 1.4 mmol) and but-3-yn-2-one (94 mg, 1.4 mmol). The reaction mixture was stirred at 25° C. for 12 h. The reaction mixture was quenched with water (50 mL) and extracted with DCM (2×25 mL). The organic layer was washed with brine (20 mL), dried over anhydrous $Na_2SO_4$ and concentrated under reduced pressure. The residue was purified by column chromatography (eluting with PE/EA=10/1) to get desired product (90 mg, 35% yield) as yellow solid. LC-MS: m/z 267 $[M+H]^+$.

Step 3

To a solution of methyl(triphenyl)phosphonium bromide (241 mg, 675 μmol) in THF (10 ml) was added butyllithium (43.3 mg, 675 μmol) dropwise under $N_2$ at −20° C. The reaction was stirred at −20° C. for 1 h. Then a solution of 1-(5-benzyloxypyrazolo[1,5-a] pyridin-3-yl) ethanone (90 mg, 338 μmol) in THF (15 ml) was added dropwise at −20° C. The reaction mixture was stirred at 10° C. for 3 h. The reaction mixture was quenched with MeOH (3 ml) and concentrated under reduced pressure. The residue was purified by prep-HPLC (eluting with PE:EA=1/1) to get crude desired product (41 mg) as yellow solid. LC-MS: m/z 265 $[M+H]^+$.

Step 4

To a solution of 5-benzyloxy-3-isopropenyl-pyrazolo[1,5-a] pyridine (600 mg, 2.3 mmol) in methanol (50 mL) was added Pd/C (60 mg). The reaction mixture was stirred at 30° C. under $H_2$ for 48 h. The reaction mixture was filtrated and concentrated under reduced pressure to get desired product (380 mg) as yellow solid. LC-MS: m/z 177 $[M+H]^+$.

Step 5

To a solution of 3-isopropylpyrazolo[1,5-a] pyridin-5-ol (650 mg, 3.7 mmol) and DIPEA (410 mg, 4.1 mmol) in DCM (15 mL) was added $Tf_2O$ (1.1 g, 4.1 mmol) under $N_2$ at 0° C. The reaction mixture was stirred at 0° C. for 2 h. The reaction mixture was washed with brine (15 mL) and dried over $Na_2SO_4$. The organic layer was filtrated, and the filtrate was concentrated to get desired product (1.1 g) as colorless oil. LC-MS: m/z 309 $[M+H]^+$.

Step 6

To a solution of (3-isopropylpyrazolo[1,5-a]pyridin-5-yl) trifluoromethanesulfonate (1.1 g, 3.4 mmol) and 4,4,5,5-tetramethyl-2-(4,4,5,5-tetramethyl-1,3,2-dioxaborolan-2-yl)-1,3,2-dioxaborolane (1.3 g, 5.1 mmol) in dioxane (10 mL) were added Pd(dppf)$Cl_2$ (249 mg, 340 μmol) and KOAc (1.0 g, 10.2 mmol). The reaction mixture was stirred at 110° C. for 2 h under $N_2$. The mixture was filtrated, and the filtrate was concentrated under reduced pressure to obtained crude desired product (950 mg) as dark solid. LC-MS: m/z 287 $[M+H]^+$.

Step 7

To a solution of 3-isopropyl-5-(4,4,5,5-tetramethyl-1,3,2-dioxaborolan-2-yl)pyrazolo[1,5-a]pyridine (950 mg, 3.3 mmol) and 2,4-dichloro-5-fluoro-pyrimidine (665 mg, 4.0 mmol) in $H_2O$ (1 mL) and 1,4-dioxane (15 mL) were added $Na_2CO_3$ (1.2 g, 10 mmol) and Pd(dppf)$Cl_2$ (242 mg, 332 μmol). The mixture was stirred under $N_2$ at 110° C. for 6 h. The mixture was concentrated under reduced pressure and the residue was purified by flash column chromatography (PE/EA with EA 0-50%) to afford desired product (650 mg, 67% yield) as yellow solid. LC-MS: m/z 291 $[M+H]^+$.

Intermediate 2

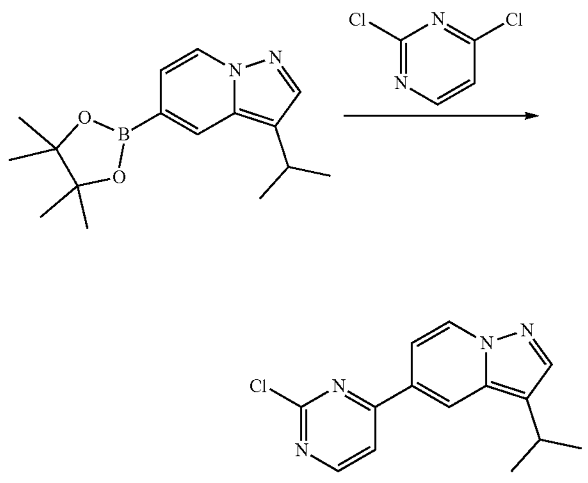

Intermediate 2

To a solution of 3-isopropyl-5-(4,4,5,5-tetramethyl-1,3,2-dioxaborolan-2-yl)pyrazolo[1,5-a]pyridine (3.5 g, 12.2 mmol) and 2,4-dichloropyrimidine (2.7 g, 18.4 mmol) in water (3 mL) and 1,4-dioxane (60 mL) were added Pd(dppf)$Cl_2$ (0.9 g, 1.2 mmol) and $Na_2CO_3$ (1.52 g, 14 mmol). The reaction mixture was stirred under $N_2$ at 110° C. for 6 h. The mixture was concentrated under reduced pressure and the residue was purified by flash column chromatography (PE with EA 0-50%) to afford desired product (2.1 g, 62% yield) as yellow solid. LC-MS: m/z 273 $[M+H]^+$.

Intermediate 3

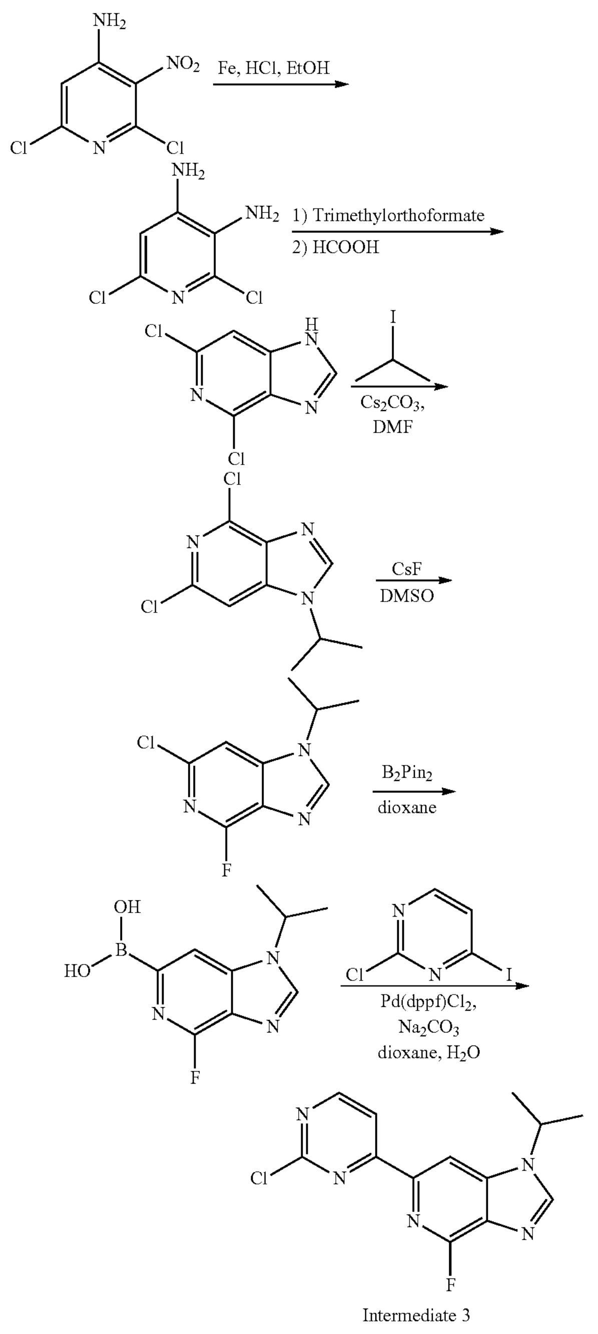

Intermediate 3

Step 1

To a mixture of 2,6-dichloro-3-nitropyridin-4-amine (1500 g, 7.2 mol) and Iron powder (1933 g, 34.6 mmol) in ethyl alcohol (45 L) and water (3 L) was added HCl (1.5 L, 12 M in $H_2O$) in water (6.5 L) drop-wise at 0° C. in 1 hour, the resulting mixture was stirred at 95° C. for 16 hours. The mixture was cooled to room temperature and then neutralized with sodium hydrogen carbonate (solid) to pH=9. The mixture was filtered and washed with ethyl acetate (500 mL). The filtrate was concentrated to remove solvent. Then the solution was extracted with ethyl acetate (9 L). The combined organic layers were washed with brine (1 L), dried over anhydrous sodium sulfate and filtered. The filtrate was concentrated to give 2,6-dichloropyridine-3,4-diamine (1200 g) as yellow solid.

Step 2

The solution of 2,6-dichloropyridine-3,4-diamine (1200 g, 6.74 mol) in triethoxy methane (3 L) was stirred under nitrogen atmosphere at 140° C. for 28 hours. The reaction was concentrated. Formic acid (1.5 L) was added. The resulting mixture was stirred at 120° C. for 2 hours. The solution was concentrated to give a residue, which was triturated with petroleum ether/ethyl acetate (1/1, 400 mL) to give 4,6-dichloro-1H-imidazo[4,5-c]pyridine (1360 g) as yellow solid.

Step 3

The mixture of 4,6-dichloro-1H-imidazo[4,5-c]pyridine (1360 g, 5.8 mol), $K_2CO_3$ (5680 g, 17.4 mol) and 2-iodo-propane (3951 g, 23.2 mol) in DMF (5 L) was stirred under nitrogen atmosphere at 20° C. for 24 hours. Ethyl acetate (40 L) was added to the reaction and the mixture was filtered. The filtrate was concentrated to give a residue, which was purified by silica gel column (petrol ether/ethyl acetate from 3:1 to 1:1) to give desired product (710 g) as yellow solid.

Step 4

To the mixture of 4,6-dichloro-1-isopropyl-imidazo[4,5-c] pyridine (250 mg, 1.1 mmol) in DMSO (10 mL) was added CsF (510 mg, 3.4 mmol), then the mixture stirred at 140° C. for 1.5 hours. The resulting mixture were poured into water (100 mL) and extracted with EA (3×30 mL). The combined organic layers were dried over $Na_2SO_4$ and filtered. The filtrate was concentrated. The residue was purified by flash column (80 g 200-300 mesh sic-gel, PE/EA=5/1-2/1) to afford desired product (210 mg, 75% yield) as a cream white solid. LC-MS: m/z 214.1 $[M+H]^+$.

Step 5

To a solution of 6-chloro-4-fluoro-1-isopropyl-imidazo[4,5-c] pyridine (30 mg, 140 μmol) and 4,4,5,5-tetramethyl-2-(4,4,5,5-tetramethyl-1,3,2-dioxaborolan-2-yl)-1,3,2-dioxaborolane (35.6 mg, 140 μmol) in dioxane (5 mL) were added potassium acetate (41.3 mg, 421 μmol) and cyclopentyl (diphenyl) phosphane dichloropalladium iron (15.4 mg, 21.1 μmol). The mixture was degassed with $N_2$ and stirred at 110° C. for 16 hours. The mixture was filtered through a Celite pad. The filtrate was concentrated under reduced pressure to crude desired product (50 mg) as black oil, which was used directly in the next step. LC-MS: m/z 224.2 $[M+H]^+$.

Step 6

To a solution of (4-fluoro-1-isopropyl-imidazo[4,5-c] pyridin-6-yl) boronic acid (50 mg, 224 μmol) and 2-chloro-4-iodo-pyrimidine (53.9 mg, 224 μmol) in dioxane (3 mL) were added Pd(dppf)$Cl_2$ (24.6 mg, 33.6 μmol) and KOAc (66 mg, 672 μmol). The mixture was degassed with $N_2$ and stirred at 110° C. for 16 hours. The mixture was concentrated under reduced pressure. The residue was purified by flash chromatography eluting with ethyl acetate in petroleum ether 0-60% to give desired product (30 mg, 46% yield) as white solid. LC-MS: m/z) 292.1 [M+H]$^+$.

Intermediate 4

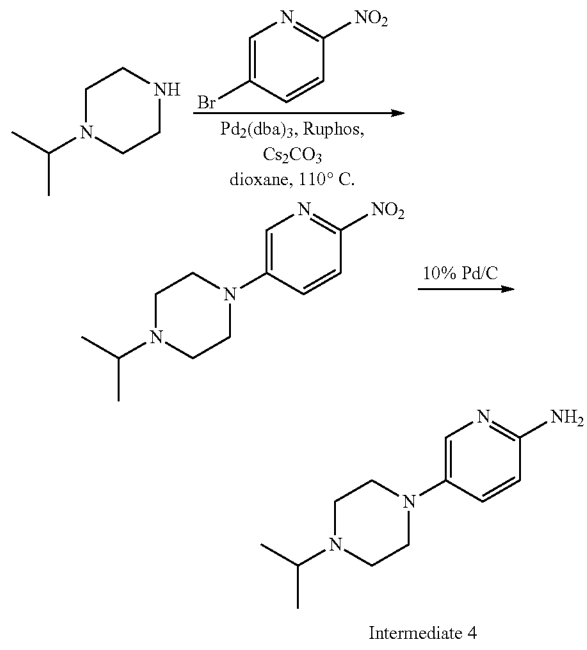

Intermediate 4

Step 1

To a solution of 5-bromo-2-nitro-pyridine (1 g, 4.9 mmol) and 1-isopropylpiperazine (631.6 mg, 4.9 mmol) in dioxane (40 mL) was added tris(dibenzylideneacetone)dipalladium (0) (451.1 mg, 492 μmol), (5-diphenylphosphanyl-9,9-dimethyl-xanthen-4-yl)-diphenyl-phosphane (570 mg, 985 μmol) and cesium carbonate (4.8 g, 14.8 mmol). Then the reaction mixture was stirred at 110° C. under $N_2$ for 3 hr. The reaction mixture was concentrated under reduced pressure and purified by silica gel chromatography eluting with ethyl acetate in petroleum ether 1-100% to afford desired product (850 mg, 68% yield) as a yellow solid. LC-MS: m/z 251.1 [M+H]$^+$.

Step 2

To a solution of 1-isopropyl-4-(6-nitro-3-pyridyl)piperazine (850 mg, 3.4 mmol) in methanol (30 mL) was added Pd/C (412 mg, 10%). Then the reaction mixture was degassed with $H_2$ for three time and stirred at 25° C. for 3 hr. The reaction mixture was filtered and then washed with methanol (20 mL). The combined solvent was concentrated under reduced pressure to give desired product (620 mg, 82% yield) as a brown solid. LC-MS: m/z 221.2 [M+H]$^+$.

Intermediate 5

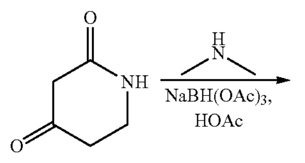

-continued

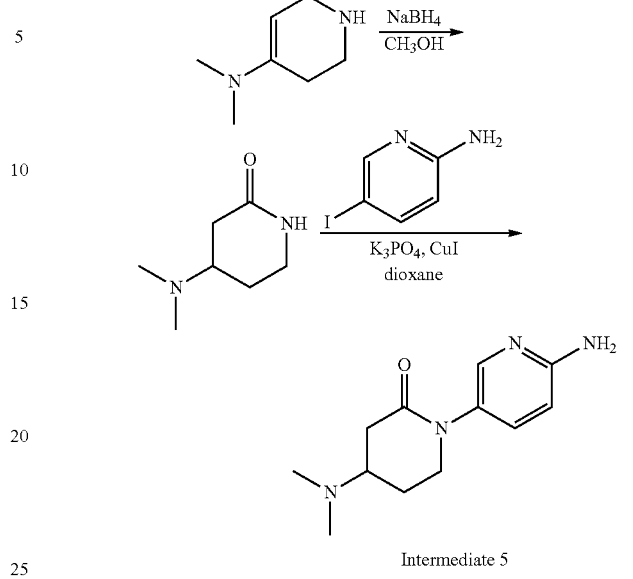

Intermediate 5

Step 1

To a mixture of piperidine-2,4-dione (2.1 g, 18.5 mmol) and N-methylmethanamine (3.4 g, 74.2 mmol) in DCM (36 mL) and THF (18 mL) was added $CH_3COOH$ (10 mL), the resulting mixture was stirred under nitrogen atmosphere at 25° C. for 3 h. Sodium triacetoxyborohydride (7.8 g, 37.1 mmol) was added to this mixture, the resulting mixture was stirred under nitrogen atmosphere at 25° C. for 12 h. The reaction was quenched with water (50 mL) and concentrated in vacuo to remove DCM and THF. The mixture was extracted with DCM (3×100 mL). The organic solution was washed with brine (20 mL). The organic phase was dried over $Na_2SO_4$, filtered and concentrated under reduced pressure to afford desired product (2.6 g), which was used in next step without any purification. LC-MS: m/z 141.2 [M+H]$^+$.

Step 2

To a mixture of 4-(dimethylamino)-2,3-dihydro-1H-pyridin-6-one (1.0 g, 7.1 mmol) in methanol (15 mL) was added sodium borohydride (539 mg, 14.2 mmol), the resulting mixture was stirred under nitrogen atmosphere at 25° C. for 12 h. The reaction was quenched with sat. $NH_4Cl$ aqueous solution (10 mL) and then concentrated in vacuo to remove MeOH. The aqueous solution was purified by reverse phase column (C18, 40 g) eluting with (MeCN/water (0.1% $NH_4OH$)=1/10) to give desired product (0.3 g, 32% yield) as light yellow solid. LC-MS: m/z 143.2 [M+H]$^+$.

Step 3

To a mixture of 4-(dimethylamino)piperidin-2-one (270 mg, 1.9 mmol), 5-iodopyridin-2-amine (1.0 g, 4.7 mmol) and potassium phosphate (1.2 g, 5.7 mmol) in dioxane (26 mL) was added (1S,2S)-N1,N2-dimethylcyclohexane-1,2-diamine (162 mg, 1.1 mmol) and CuI (108 mg, 569 μmol), the resulting mixture was stirred under nitrogen atmosphere at 110° C. for 12 h. The reaction was filtered. The filtrate was concentrated in vacuo to give the residue, which was purified by reverse phase column (C18, 20 g) eluting with (MeCN/water (0.1% $NH_4OH$)=1/10) to give desired product (272 mg, 61% yield) as a light-yellow solid. LC-MS: m/z 235.2 [M+H]$^+$.

Synthetic Example 1

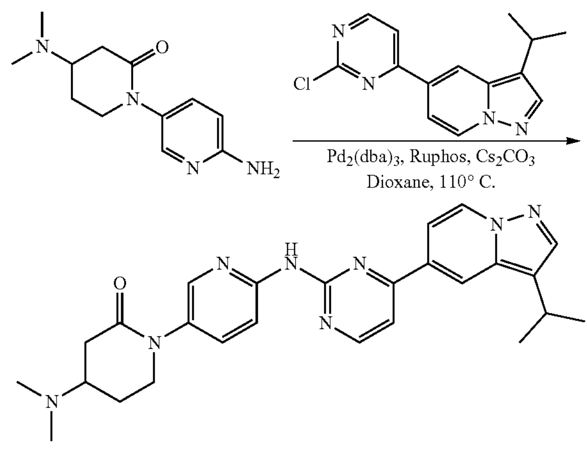

synthetic example 1

To a mixture of 1-(6-amino-3-pyridyl)-4-(dimethylamino) piperidin-2-one (30 mg, 128 μmol) and 5-(2-chloropyrimidin-4-yl)-3-isopropyl-pyrazolo[1,5-a]pyridine (38.4 mg, 140.8 μmol) in dioxane (5 mL) was added cesium carbonate (125.1 mg, 384.1 μmol), tris(dibenzylideneacetone)dipalladium(0) (11.7 mg, 12.8 μmol) and RuPhos (11.9 mg, 25.6 μmol). The resulting mixture was stirred under nitrogen atmosphere at 110° C. for 4 h. The reaction mixture was extracted with EA (20 mL). The organic phase was washed with water (3×20 mL), brine (3×20 mL) and dried over $Na_2SO_4$. The mixture was concentrated under reduced pressure and purified by flash column chromatography (DCM/MeOH=10:1) to afford desired product (23.8 mg, 39% yield) as a yellow solid. LC-MS: m/z 471.2 [M+H]$^+$.

Synthetic Examples 2 and 3

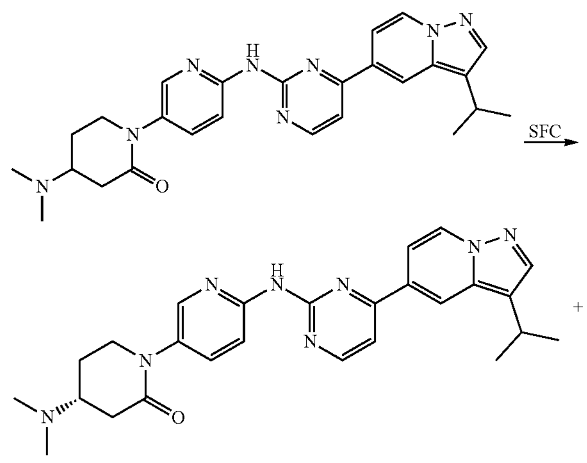

synthetic example 2

-continued

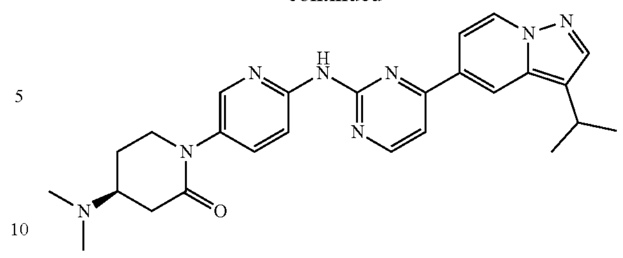

synthetic example 3

N-[5-[4-(dimethylamino)-1-piperidyl]-2-pyridyl]-4-(3-isopropylpyrazolo[1,5-a]pyridin-5-yl)pyrimidin-2-amine (210 mg, 459.9 μmol) was chiral separated by SFC with mobile phase (Hexane/EtOH/DEA=60/40/0.1) (wave length: UV 214 nm, Column: CHIRALCEL OD-H 5.0 cm I.D.×25 cm L, Flow rate: 60 mL/min) to give synthetic example 2 (44.2 mg, 21% yield) as a yellow solid (LC-MS: m/z 471.2 [M+H]$^+$. ee value >99%) and synthetic example 3 (41 mg, 19% yield) as a yellow solid (LC-MS: m/z 471.2 [M+H]$^+$. ee value=97%).

Synthetic Example 4

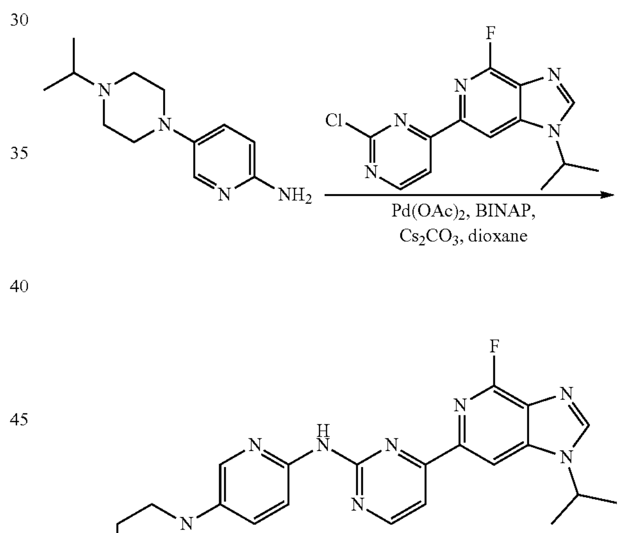

synthetic example 4

To a solution of 5-(4-isopropylpiperazin-1-yl)pyridin-2-amine (124.6 mg, 565 μmol) and 6-(2-chloropyrimidin-4-yl)-4-fluoro-1-isopropyl-imidazo[4,5-c]pyridine (150 mg, 514 μmol) in dioxane (15 mL) was added $Pd_2(dba)_3$ (47.1 mg, 51 μmol), RuPhos (47.9 mg, 102 μmol) and $Cs_2CO_3$ (502.6 mg, 1.5 mmol). The mixture was stirred at 110° C. under $N_2$ for 3 hr. The reaction mixture was concentrated under reduced pressure. The residue was purified by silica gel chromatography eluting with MeOH in DCM 0-10% to afford desired product (107.2 mg, 43% yield) as a yellow solid. LC-MS: m/z 476.2 [M+H]$^+$.

Biological Example 1. Assay for Inhibition of CDK4/CyclinD1

The CDK4 enzyme assay for $IC_{50}$ determination was performed as follows. Microfluidic kinase detection technology (Caliper) was used to monitor the phosphorylation of peptide substrate by CDK4/CyclinD1. The total reaction volume was 15 μL containing buffer A (100 mM HEPES (pH 7.5), 0.1% BSA, 0.01% Triton X-100, 1 mM DTT, 10 mM $MgCl_2$, 10 μM Sodium Orthovanadate, 10 μM Beta-Glycerophosphate), 200 μM ATP, 1 nM CDK4/CyclinD1 (Thermofisher, PR8064A), 1 μM FL-34 (5-FAM-RRRFRPASPLRGPPK), and the test compound at appropriate dilutions in DMSO. All components were added to the 384-well plate (Corning, 4514), and incubated at Room Temperature for 3 hours. The reaction was terminated by addition of 15 μL Stop Buffer (180 mM HEPES (pH 7.5), 20 mM EDTA, Coating-3 reagent (PerkinElmer, 760050)). The plate was then loaded on Caliper EZ Reader (EZ Reader II, PerkinElmer, HD-4HYSG2772), and the reaction mixtures including substrate and product were sipped into the microfluidic chip for separation and detection. The $IC_{50}$ values of the test compound were determined by fitting the inhibition curves by 4 parameter sigmoidal dose-response model using the Xlfit5/GraphPad Prism 5 software.

Biological Example 2. Assay for Inhibition of CDK6/CyclinD3

The CDK6 enzyme assay for $IC_{50}$ determination was performed as follows. Microfluidic kinase detection technology (Caliper) was used to monitor the phosphorylation of peptide substrate by CDK6/CyclinD3. The total reaction volume is 15 μL containing buffer A (100 mM HEPES (pH 7.5), 0.1% BSA, 0.01% Triton X-100, 1 mM DTT, 10 mM $MgCl_2$, 10 μM Sodium Orthovanadate, 10 μM Beta-Glycerophosphate), 300 μM ATP, 2 nM CDK6/CyclinD3 (Carna, 04-107), 1 μM FL-34 (5-FAM-RRRFRPASPLRGPPK), and the test compound at appropriate dilutions in DMSO. All components were added to the 384-well plate (Corning, 4514), and incubated at Room Temperature for 3 hours. The reaction was terminated by addition of 15 μL Stop Buffer (180 mM HEPES (pH 7.5), 20 mM EDTA, Coating-3 reagent (PerkinElmer, 760050)). The plate was then loaded on Caliper EZ Reader (EZ Reader II, PerkinElmer, HD-4HYSG2772), and the reaction mixtures including substrate and product were sipped into the microfluidic chip for separation and detection. The $IC_{50}$ values of the test compound were determined by fitting the inhibition curves by 4 parameter sigmoidal dose-response model using the Xlfit5/GraphPad Prism 5 software.

Biological Example 3. Assay for Inhibition of CDK2/CyclinE1

The CDK2 enzyme assay for $IC_{50}$ determination was performed as follows. Microfluidic kinase detection technology (Caliper) was used to monitor the phosphorylation of peptide substrate by CDK2/CyclinE1. The total reaction volume was 15 μL containing buffer A (100 mM HEPES (pH 7.5), 0.1% BSA, 0.01% Triton X-100, 1 mM DTT, 10 mM $MgCl_2$, 10 μM Sodium Orthovanadate, 10 μM Beta-Glycerophosphate), 100 μM ATP, 5 nM CDK2/CyclinE1 (SignalChem, C29-18G), 5 μM FL-18 (5-FAM-QSPKKG-NH2), and the test compound at appropriate dilutions in DMSO. All components were added to the 384-well plate (Corning, 4514), and incubate at Room Temperature for 3 hours. The reaction was terminated by addition of 15 μL Stop Buffer (180 mM HEPES (pH 7.5), 20 mM EDTA, Coating-3 reagent (PerkinElmer, 760050)). The plate was loaded on Caliper EZ Reader (EZ Reader II, PerkinElmer, HD-4HYSG2772), and the reaction mixtures including substrate and product were sipped into the microfluidic chip for separation and detection. The $IC_{50}$ values of the test compound were determined by fitting the inhibition curves by 4 parameter sigmoidal dose-response model using the Xlfit5/GraphPad Prism 5 software.

The $IC_{50}$ values of each exemplified compound against CDK2, CDK4 and CDK6 are provided in the synthetic examples below. The $IC_{50}$ values are indicated as "A," "B," "C," and "D," for values less than or equal to 10 nM; less than or equal to 100 nM; less than or equal to 1 μM; and greater than 1 μM, respectively.

Biological Example 4. Anti-Proliferation Assay in T47D Cell

T47D is a human breast cancer cell line commonly used in biomedical research involving the hormonal expression of cancer cells. T47D cells are distinct from other human breast cancer cells in that their progesterone receptors (PR) are not regulated by estradiol, a hormone that is abundant within the cells themselves. T47D cells have been employed in studies of the effects of progesterone on breast cancer and the corresponding transcriptional regulation caused by introduced drugs. The cells have been noted to be extremely resistant to estrogens and antiestrogens.

T47D breast cancer cells from American Type Culture Collection (ATCC, HTB-133) were plated at 3000 cells/well in 96-well plates, and were incubated in RPMI 1640 medium (Gibco, 31800105) with 10% Fetal Bovine Serum (FBS, Biowest, FB-1058) at 37° C., 5% $CO_2$. After overnight incubation, baseline values were measured of the samples from one plate using Cyquant reagent (Invitrogen, C35011) following manufacturer's recommendations. Cells were incubated with the detection reagent for 1 hour at 37° C., and then the fluorescence was measured with excitation at 485 nm and emission at 535 nm using Spectra Max M5 (Molecular Devices, HD-4HYSG3196). Other plates were dosed with compounds at a ten-point dose concentration from 10 μM to 0.51 nM in a 3-fold dilution scheme. On day 6 after compound addition, Cyquant reagent was added and the fluorescence was measured using Spectra Max M5. The $IC_{50}$ values of the test compound's anti-proliferation activity were determined from the baseline subtracted viability readout curve using Xlfit5/GraphPad Prism 5 software.

Biological Example 5. Inhibition of Phosphorylation of Retinoblastoma Protein (pRb) in T47D Cell T47D breast cancer cells from American Type Culture Collection (ATCC, HTB-133) were plated at 40,000 cells/well in 96-well plates, and were incubated in RPMI 1640 medium (Gibco, 31800105) with 10% Fetal Bovine Serum (FBS, Biowest, FB-1058). Cells were then allowed to adhere overnight at 37° C., 5% $CO_2$. The following day, compounds were titrated in a 3-fold dilution scheme, and the highest compound concentration tested was 10 μM. After 24 hours incubation with compounds, cells were lysed in ice-cold lysis buffer containing phosphatase inhibitor cocktail and 1 mM PMSF. Cell lysates (50 μL/well) were then transferred to ELISA plates (pRb Ser807/811 ELISA kit, Cell Signaling, 13152 or pRb Ser780 ELISA kit, Cell Signaling, 13016)).

Plates were incubated overnight at 4° C., with constant slow speed shaking. After incubation, plates were washed following manufacturer's recommendations, and then 100 μL reconstituted detection antibody was added to each well and incubated for 1 hour at 37° C. After incubation, plates were washed, and then 100 μL reconstituted HRP-linked secondary antibody was added to each well and incubated for 30 mins at 37° C. After incubation, plates were washed. Then, 100 μL TMB substrate was added to each well and incubated for 10 min at 37° C. or 30 min at 25° C. Finally, 100 μL of STOP solution was added to each well and mixed gently for a few seconds. Plates were read on the Envision plate reader (PerkinElmer, 2104-0010) using the 96-well luminescence mode. $IC_{50}$ values were calculated using 4 parameter sigmoidal dose-response model of Xlfit5/GraphPad Prism 5 software.

The cellular data obtained from biological examples 4 and 5 are listed in the Table A below. The $IC_{50}$ values are indicated as "++++", for values less than or equal to 100 nM; "+++", for values less than or equal to 500 nM; "++", for values less than or equal to 1 μM; and "+", for values greater than 1 μM, respectively.

TABLE A

| Synthetic Example | CDK4 $IC_{50}$ | CDK6 $IC_{50}$ | CDK2 $IC_{50}$ | T47D $IC_{50}$ | Phospho T47D Ser807 $IC_{50}$ |
|---|---|---|---|---|---|
| 1 | A | A | B | ++++ | ++++ |
| 2 | A | B | B | ++++ | ++++ |
| 3 | A | A | A | ++++ | ++++ |
| 4 | A | B | C | ++++ | ++++ |

The invention claimed is:

1. A compound represented by the following structural formula:

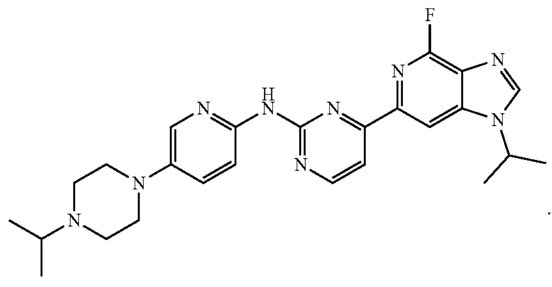 [SMILES: CC(C)N1CCN(c2ccc(Nc3nccc(-c4cc5c(ncn5C(C)C)c(F)n4)n3)nc2)CC1]

2. A pharmaceutical composition comprising an effective amount of the compound of claim 1, and a pharmaceutically acceptable carrier.

* * * * *